United States Patent [19]

Lindow et al.

[11] Patent Number: 4,748,335
[45] Date of Patent: May 31, 1988

[54] METHOD AND APARATUS FOR DETERMINING SURFACE PROFILES

[75] Inventors: James T. Lindow, Saratoga; Simon D. Bennett; Ian R. Smith, both of Los Gatos, all of Calif.

[73] Assignee: SiScan Systems, Inc., Campbell, Calif.

[21] Appl. No.: 752,160

[22] Filed: Jul. 3, 1985

Related U.S. Application Data

[63] Continuation-in-part of Ser. No. 725,082, Apr. 19, 1985.

[51] Int. Cl.⁴ ............................................. G01N 21/88
[52] U.S. Cl. .................................... 250/572; 356/376
[58] Field of Search ............... 250/571, 572, 560, 563; 356/244, 376; 350/507, 508

[56] References Cited

U.S. PATENT DOCUMENTS

| T102,104 | 8/1982 | Kirk et al. | 356/387 |
|---|---|---|---|
| 4,112,309 | 9/1978 | Nakazawa et al. | 250/560 |
| 4,194,127 | 3/1980 | Schmidt | 250/572 |
| 4,198,571 | 4/1980 | Sheppard | 250/571 |
| 4,350,884 | 9/1982 | Vollath | 250/204 |
| 4,473,750 | 9/1984 | Oshida et al. | 250/560 |
| 4,505,585 | 3/1985 | Yoshikawa et al. | 356/237 |
| 4,600,832 | 7/1986 | Grund | 250/201 |

FOREIGN PATENT DOCUMENTS

| 0094835 | 11/1983 | European Pat. Off. |
| 2741807 | 3/1979 | Fed. Rep. of Germany. |
| 1206668 | 9/1970 | United Kingdom. |
| 2144537 | 3/1985 | United Kingdom. |

OTHER PUBLICATIONS

Ichioka et al., "Digital Scanning Laser Microscope", Applied Optics, vol. 24, No. 5, pp. 691–696, 1 Mar. 1985.
Hamilton et al., "Surface Profile Measurement Using the Confocal Microscope", Journal of Applied Physics, vol. 53, No. 7, pp. 5320–5322, Jul. 1982.
Marsman et al., "Mechanical Scan System for Microscopic Applications", RCU. Sci. Instrum., vol. 54, No. 8, pp. 1047–1052, Aug. 1983.
Brakenhoff et al., "Confocal Scanning Light Microscopy with High Aperture Immersion Lenses", J. Microsc., vol. 117, pp. 219–232 (1979).
Brakenhoff, "Imaging Modes in Confocal Scanning Light Microscopy (CSLM)", J. Microsc., vol. 117, pp. 233–242 (1979).

Primary Examiner—Eugene R. LaRoche
Assistant Examiner—Robert J. Pascal
Attorney, Agent, or Firm—Robert S. Kelly

[57] ABSTRACT

A system for determining surface profiles of specimens such as semiconductor wafers includes a drive for mounting the wafer for oscillatory movement along a line and an optical imaging system overlying the wafer for focusing a beam on a small sport on the wafer and including a photodetector for detecting the reflected sport from the wafer. The spot is scanned along the line on the wafer while the focal depth of the imaging system is progressively changed while the photodetector and connected digital circuitry generate a plurality of spaced output signals for each scan along the line so that data comprised of a series of spaced signals are provided at a plurality of focus levels extending through the surface profile of the wafer. Computer means are provided for analyzing the data and providing a graphical output of the surface profile.

42 Claims, 9 Drawing Sheets fig_1

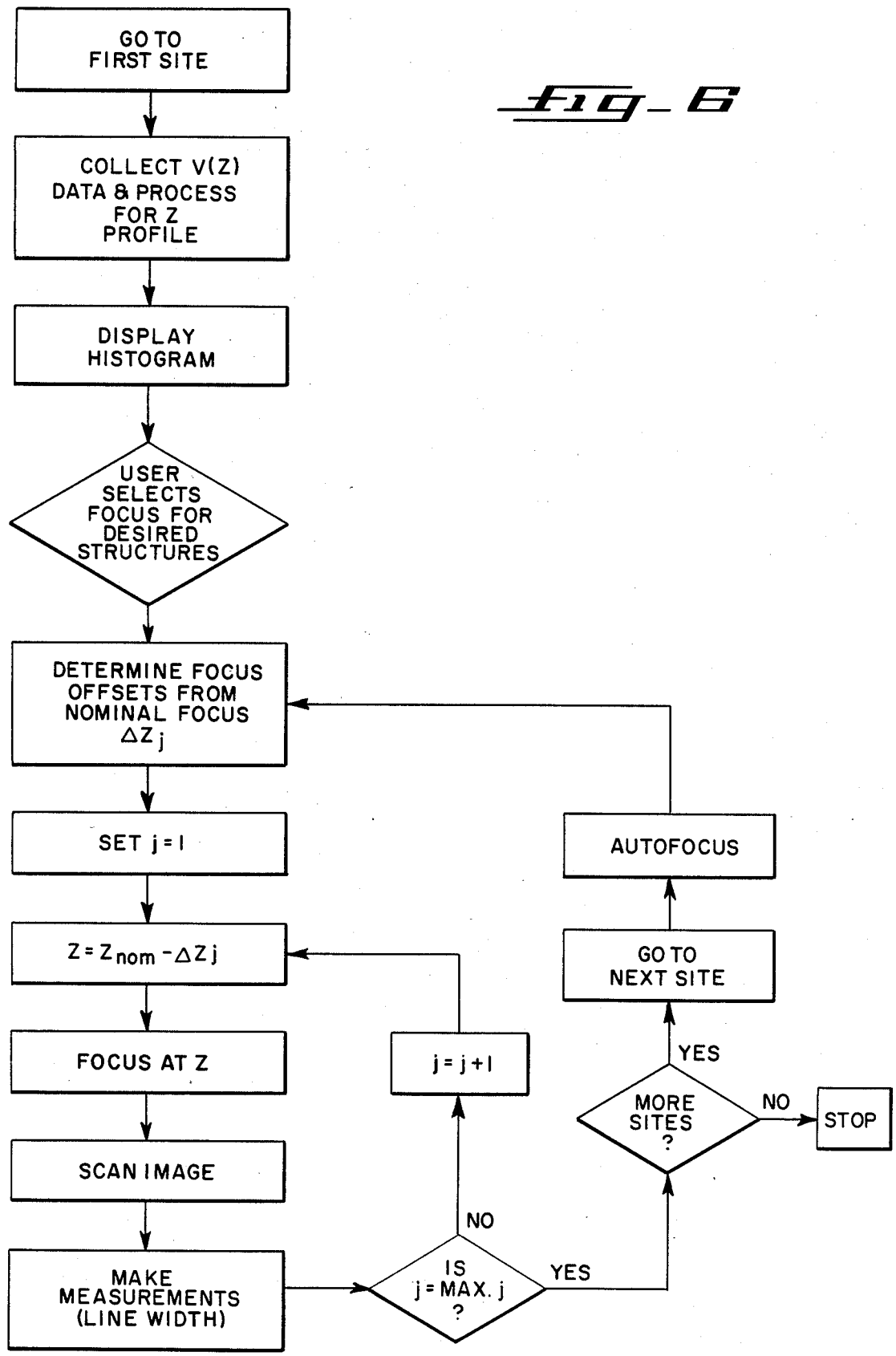
fig_6

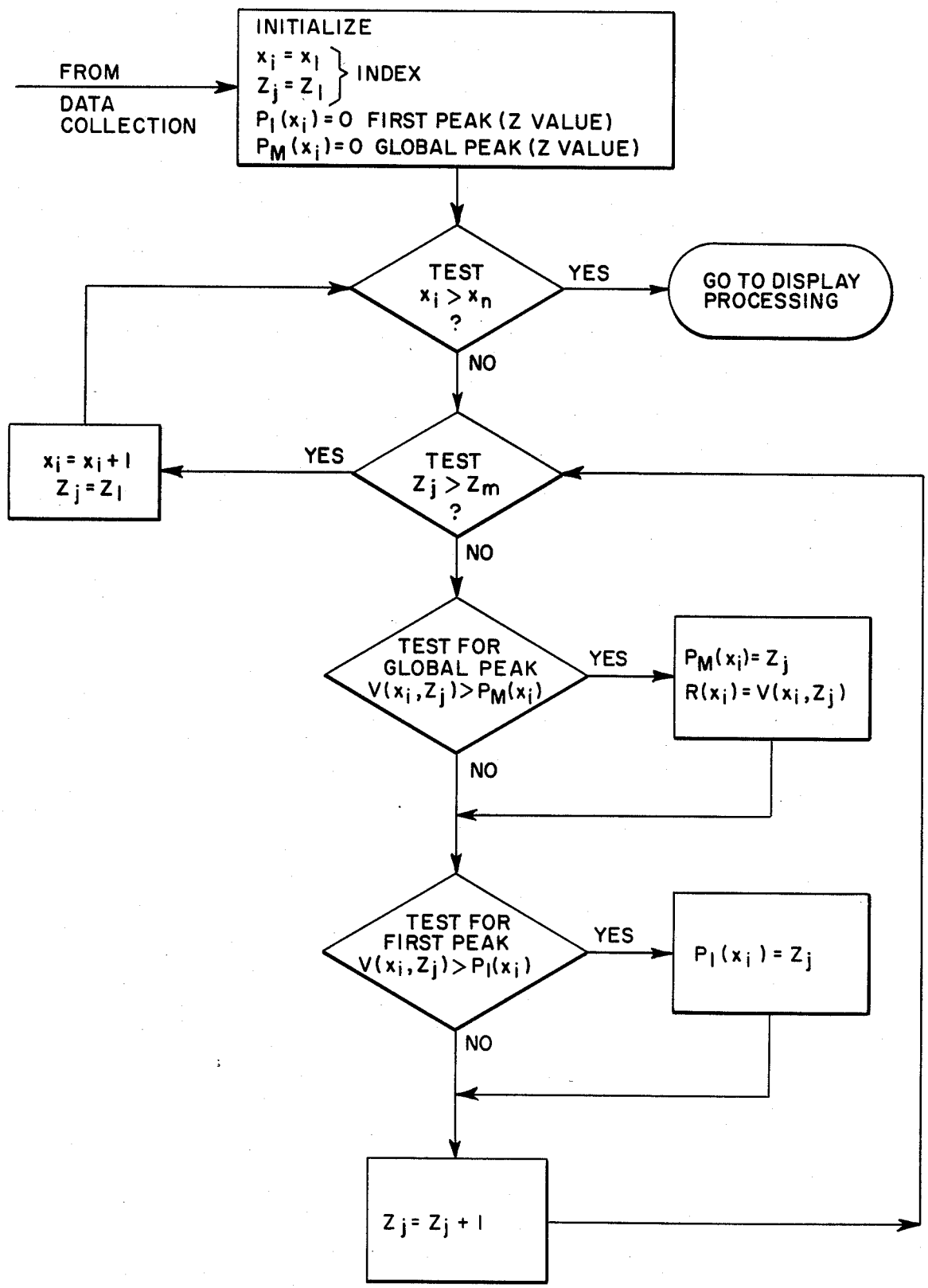
fig_7B

Fig. 8
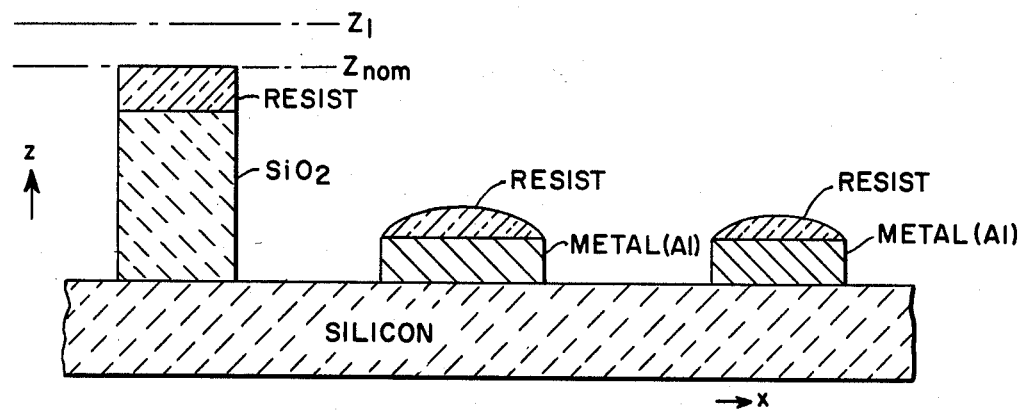
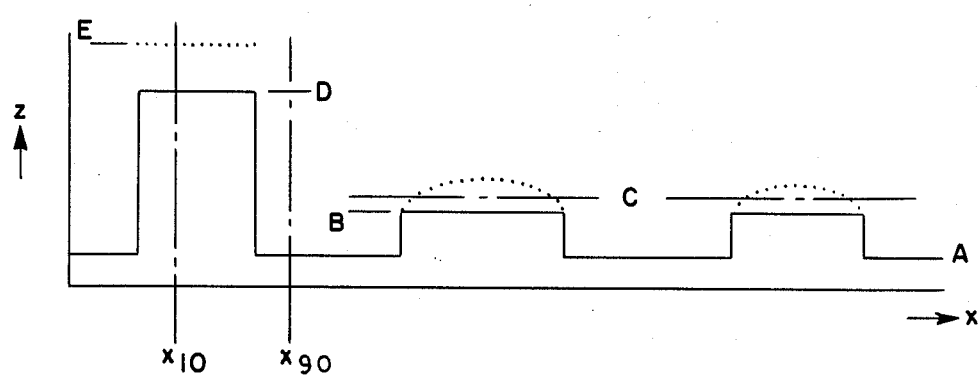
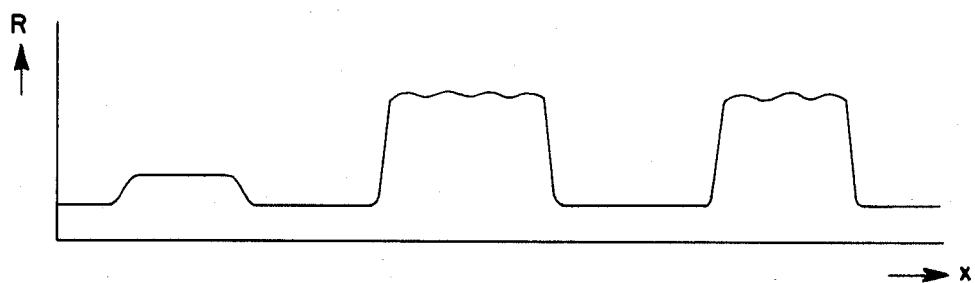
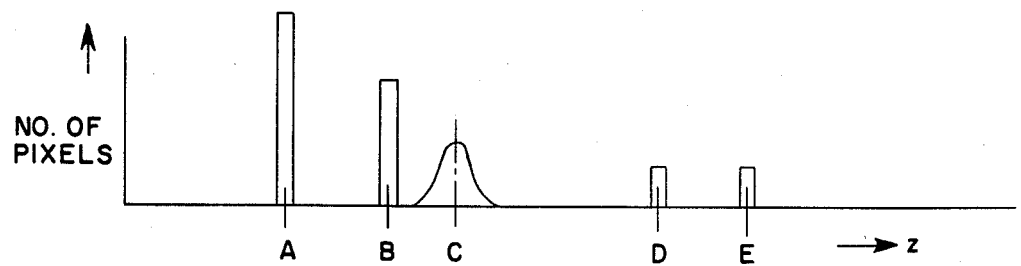

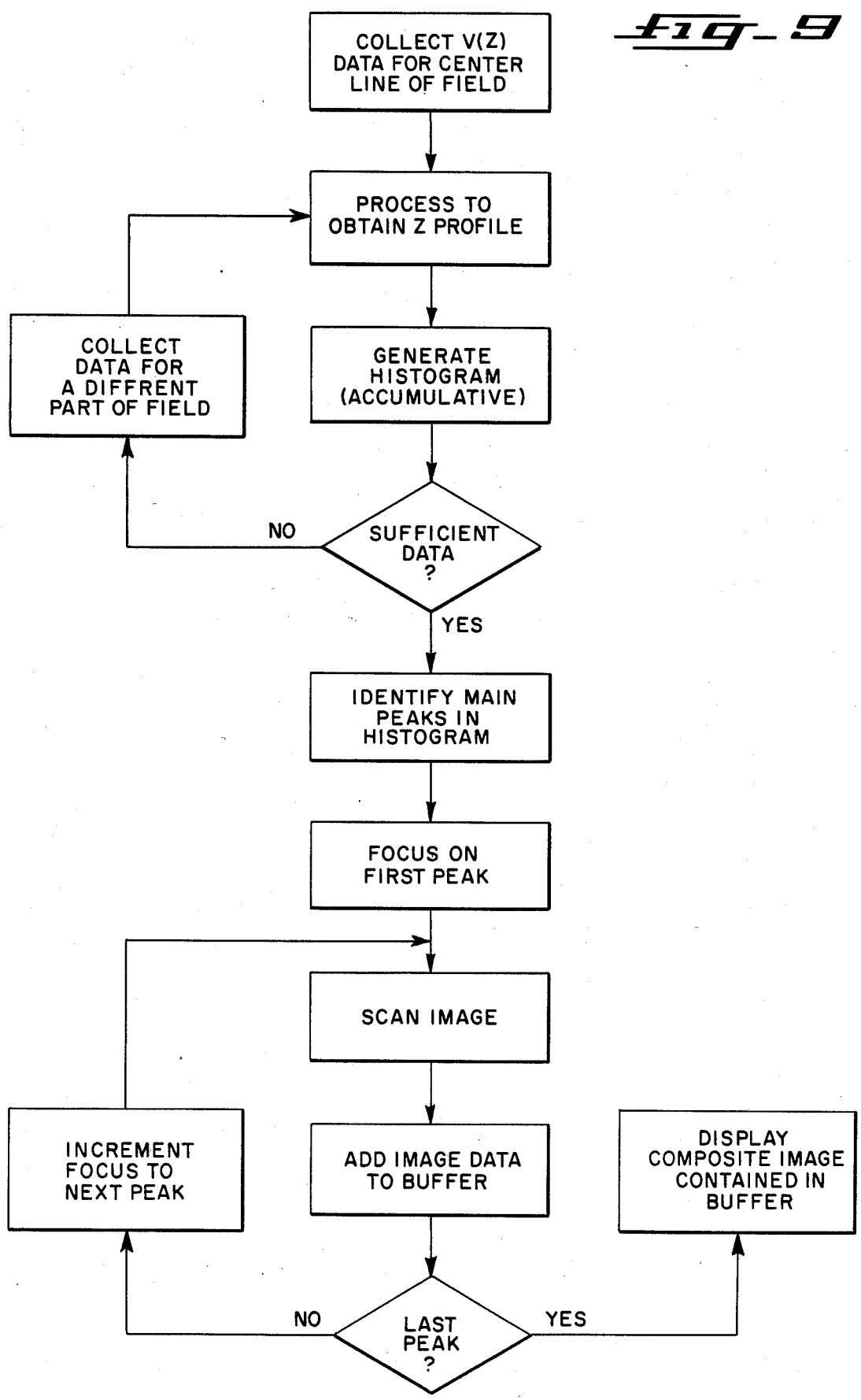

METHOD AND APARATUS FOR DETERMINING SURFACE PROFILES

CROSS REFERENCE TO RELATED APPLICATION

This application is a continuation-in-part of U.S. patent application Ser. No. 725,082, filed Apr. 19, 1985, by James T. Lindow et. al., and entitled Semiconductor Wafer Scanning System.

BACKGROUND OF THE INVENTION

1. Field of the Invention

The present invention pertains to systems for scanning surface patterns on specimens such as semiconductor wafers or the like, and more particularly, it pertains to methods and apparatus for accurately obtaining a cross-sectional surface profile of such specimens.

2. Description of the Prior Art

In the inspection of semiconductor wafers or the like to detect surface pattern defects, a variety of techniques have been utilized that take advantage of various forms of microscopes, optical, acoustical, and scanning electron types. In optical imaging systems generally, devices similar to T.V. cameras have been utilized wherein electromagnetic radiation is reflected from a relatively large spot on the wafer and processed through an optical system and imaging camera to provide a multi-intensity image which, either digitally or by analog means, can be recreated on an appropriate output device, such as a CRT.

The inspection of semiconductor wafers typically provides a means whereby certain processing defects can be detected or whereby linewidth measurements can be made so as to determine whether or not the manufacturing process has been performed correctly. Since the tolerance limits for the dimensions which must be detected and measured accurately are in the micron or even submicron range, microscope imaging systems generally require a high degree of imaging resolution.

In certain prior art wafer inspection systems, laser beams are focused through optical systems having a very narrow depth of field. Then, by scanning the laser beam along the top surface of the semiconductor wafer, the patterned lines, or patterns on the wafer, can be measured by utilizing special detector devices to denote the edges of such lines by measuring the scattered light therefrom. It has been generally recognized that with such wafer scanning systems of the aforedescribed type the beam focus level can be adjusted as it is scanned across the wafer so as to track the changing surface level thereof by noting when the reflected image moves slightly out of focus and by adjusting the spacing between the wafer and the optical system (by moving either one relative to the other) so as to continually maintain the reflective surface of the wafer at the proper focus. Prior art patents which describe such scanning systems include U.S. Pat. No. 4,505,585 to Yoshikawa et al and United States Defensive Publication T102,104 to Kirk et al.

SUMMARY OF THE INVENTION

With the present invention, methods and apparatus are provided for systematically obtaining the cross-sectional profile within a given area on the semiconductor wafer surface. The information provided by this profile can thereafter be effectively utilized to make the conventional pattern linewidth measurements with a generally greater degree of accuracy than that provided by the systems of the prior art. Also, the profile provides the necessary information to determine at what specific levels the given wafer area should be scanned such that the entire area of the wafer can be rapidly scanned only at such selected levels to provide all of the relevant information necessary, reducing the processing times and digital storage capacities required.

With the method and apparatus of the present invention. an optical imaging system is provided to both project a sharply defined beam onto a small spot upon the wafer surface and to detect the image of the reflected spot with respect to a measurable characteristic of the reflected beam indicative of the reflective surface at or near the focal plane. The optical imaging system and the wafer are relatively moved in a plane generally parallel to the surface of the wafer so that the projected spot scans a line across a portion or given area of the wafer, and means are provided for recording and storing a signal representative of the measurable characteristic at a plurality of very closely spaced positions along the scan line. The focus level of the imaging system is successively changed by moving the wafer and imaging system closer together or further apart after each pass along a scan line until a plurality of scans have been made completely passing through the relevant surface detail of the wafer. Then, for each single recording position along the scan line, that focus level of the system is determined wherein a signal most characteristic of a surface indication [e.g.. a maximum relected intensity signal) was obtained. The serial accumulation of the thus determined focus levels for each of the closely spaced positions along the scan line represents a cross-sectional profile of the surface of the wafer along the scan line.

This surface profile information can then be utilized for directly making a pattern linewidth measurement, or the information can be used for selecting the particular surface levels at which the optical system needs to be automatically focused during subsequent scans throughout the particular portion or area on the wafer. This permits the selected wafer area to be thoroughly scanned and three-dimensional images to be produced.

BRIEF DESCRIPTION OF THE DRAWINGS

FIG. 6 is a flow chart depicting the programming for the computer which controls the various operative components of the system of the present invention.

FIGS. 7A, 7B, and 7C collectively comprise a flow chart depicting a subroutine of the program of FIG. 6 for respectively collecting, processing and displaying the data for the cross-sectional profile.

FIG. 8 is a cross-sectional illustration of a portion of a scanned semiconductor wafer surface and the corresponding profile and reflectivity displays and focal level histogram obtained with the system of the present invention.

FIG. 9 is a flow chart depicting the programming for the system of the present invention wherein a "superfocus" image is obtained and displayed.

DESCRIPTION OF THE PREFERRED EMBODIMENT

Figure 1:
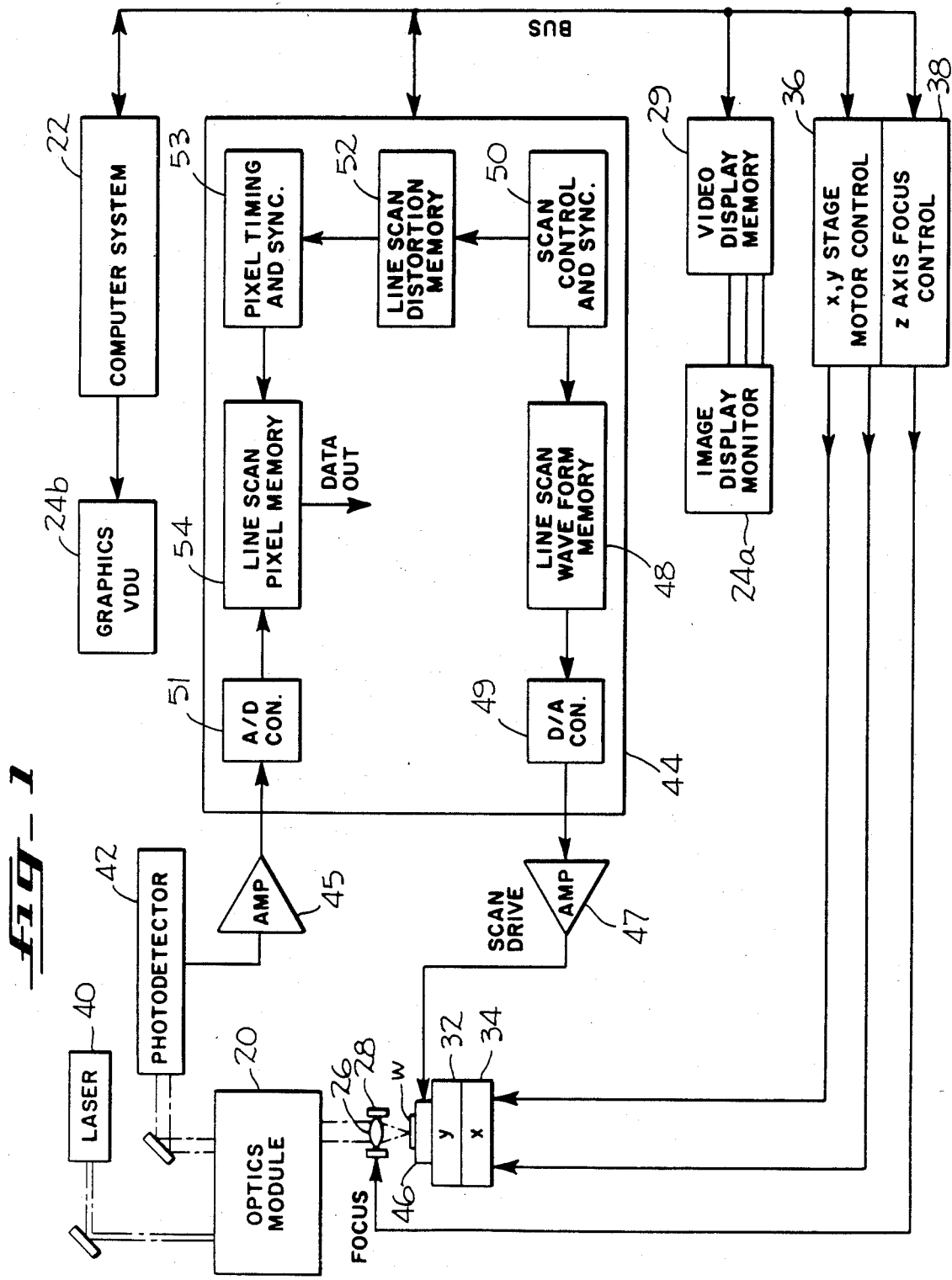
FIG. 1 is a diagrammatic representation of the semiconductor wafer scanning and profiling system of the present invention.

The profiling technique of the present invention is adapted to be carried out by and to be useful with a wafer scanning system such as shown in FIG. 1 and more specifically described and claimed in our copending U.S. patent application Ser. No. 725,082, filed Apr. 19, 1985, and entitled "Semiconductor Wafer Scanning System". The disclosure of this prior application is herein incorporated by reference into the present application, and reference to such application may be had for a more detailed explanation of the appratus of the present invention and the method of operation thereof.

Referring now to FIG. 1, which very schematically illustrates the mechanical apparatus of the present invention and, in block diagram form, the circuitry of the present invention, it will be seen that an optics module 30 is provided to focus a sharply defined beam from a laser source 40 on a small spot upon are underlying semiconductor wafer, w. The optics module comprises a confocal optical imaging system which is controlled by and provides data information signals to a computer system 22. The computer outputs information to various display units including an image display monitor 24a (where the "superfocus" image of the entire scanned area is displayed) and a graphics video display unit 24b (where the profiles, graphs and histograms are displayed). The surface of the semiconductor wafer, w, to be inspected by the system underlies the optical imaging system and extends in a plane generally perpendicular to the projected beam. The wafer is arranged to be moved in this plane in x and y orthogonal directions by x and y stages 34, 32, respectively and also by a vibratory scanning mechanism 46 aligned for movement in the x direction. Under the control of appropriate signals from the computer system 22, the x and y stages are driven by conventional motor control circuitry 36. Movement in the z direction, i.e., in a direction generally parallel to the light beam projected from laser source 40, is accomplished by a focus control mechanism 28 which shifts an objective lens 26 (the last element of the optical system) over very small vertical distances in order to change the focal plane of the optical system. The focus control mechanism is operated from the computer system through a focus control signal from conventional control circuitry 38 to shift the lens 26 up or down. The beam from laser source 40 is sharply focused with a very narrow depth of field, and it is adapted to be reflected from a surface on wafer w (if one is present) at the focal plane back through the optical system to a photodetector 42. The signal from the photodetector is sampled and digitized by the control circuitry 41 and transmitted to the computer system 22 and represents the intensity of the reflected light received from the projected spot on the surface of wafer w. These digital signals are provided as a function of the focus level, z, and also as a function of separate, closely spaced positions in the x-y plane. Since the optical system has a very narrow depth of field, reflected intensity peaks as the focal plane coincides with an underlying reflective surface and drops off rather sharply as the wafer surface is moved away from the focal plane. Thus the height of the wafer at any particular planar (x,y) position thereon can be readily detected by operating the focus control mechanism 28 to achieve a maximum output signal representing the intensity of the reflected light. It is upon this fundamental principle that the present invention is based. The computer system 22 tracks both the x, y positions of the wafer with respect to the beam and the z level focal plane location of the beam and coordinates this information with the intensity signals from photodetector 42 in order to provide a three dimensional output representation of the portion of the wafer that is scanned.

As pointed out previously, the wafer, w, is moved in the horizontal plane by x and y stages 34 and 32, respectively, which are controlled by x, y stage motor control circuitry 36 under the monitoring of the computer system 22. The stages 32, 34 comprise conventional precision translation tables provided with optical position encoders for submicron resolution and accuracy. The motor control circuitry 36 is also conventional in nature providing drive signals for moving the stages and including A/D circuitry for receiving and processing the signals from the position encoders so as to accurately monitor the position of the wafer at any given instant. The z-axis focus control circuitry 38 provides an output voltage for the focus control mechanism 28 which, in the present instance, comprises a piezoelectric crystal that expands or contracts in the vertical plane and responds to the applied voltage to shift the relative vertical position of objective lens 26.

The control circuitry 44 for the entire system is adapted to receive a continuous input light intensity signal from the photodetector 42 through amplifier 45 and synchronize this data with the scanner 46 position information. The control circuitry 44 also serves to output a scan drive signal (a sinosoidal wave form) to the vibratory scanning mechanism 46 through an amplifier 47. The scanning mechanism 46 vibrates the wafer rapidly in the x direction. The stage, or linear translator, 32, may be adapted to simultaneously move the wafer w slowly in the y direction during the vibratory scanning movement in the x direction when it is desired to provide a two dimensional planar scan at a particular level on the wafer. By scanning at a plurality of levels, a three dimensional scan is obtained, such three dimensional scanning of an entire area (or site) on a wafer being explained in detail in the aforementioned copending U.S. patent application Ser. No. 725,082. As will be explained in greater detail hereinafter, the basic profiling technique of the present invention requires that the scanner 46 move only in the x direction making a repeated number of scans over the same line on the wafer while incrementally changing the level of lens 26 through focus control mechanism 28 after each individual scan.

In the control circuitry 44 it will be seen that the scan drive voltage is provided digitally out of the line scan wave form memory circuitry 48 and that a D/A converter 49 converts the digital signals to an analog signal for appropriate amplification by the amplifier 47. The memory 48 is addressed by scan control and synchronization circuitry 50. The incoming analog signal from the photodetector 42 is converted to a digital signal by A/D converter 51. Since the scanning mechanism 46 carrying the wafer, w, will move at a varying linear velocity as the wafer, w, is scanned, the timing of the digital photodetector signal sampling is such that the recorded digital signal information will correspond to generally uniformly spaced positions along the scan line on the wafer so that a distortion free image of the wafer can be created in the ouput devices 24a and 24b. In order to accomplish this objective, a line scan distortion memory 52 is provided to control the timing between the samples. The timing information from memory 52 is utilized by pixel timing and synchronizing circuitry 53 which controls a line scan pixel memory 54 that accepts and stores the digital input signals at the appropriate times. Each sampled signal (from the photodetector) corresponds to a pixel which is a representation of a very small incremental area on the wafer with the sampled signal at the time being a measurement of the reflected light from such incremental area. For a further and more complete description of the control circuitry 44 reference is again made to our aforementioned copending U.S. patent application Ser. No. 725,082.

Figure 2:
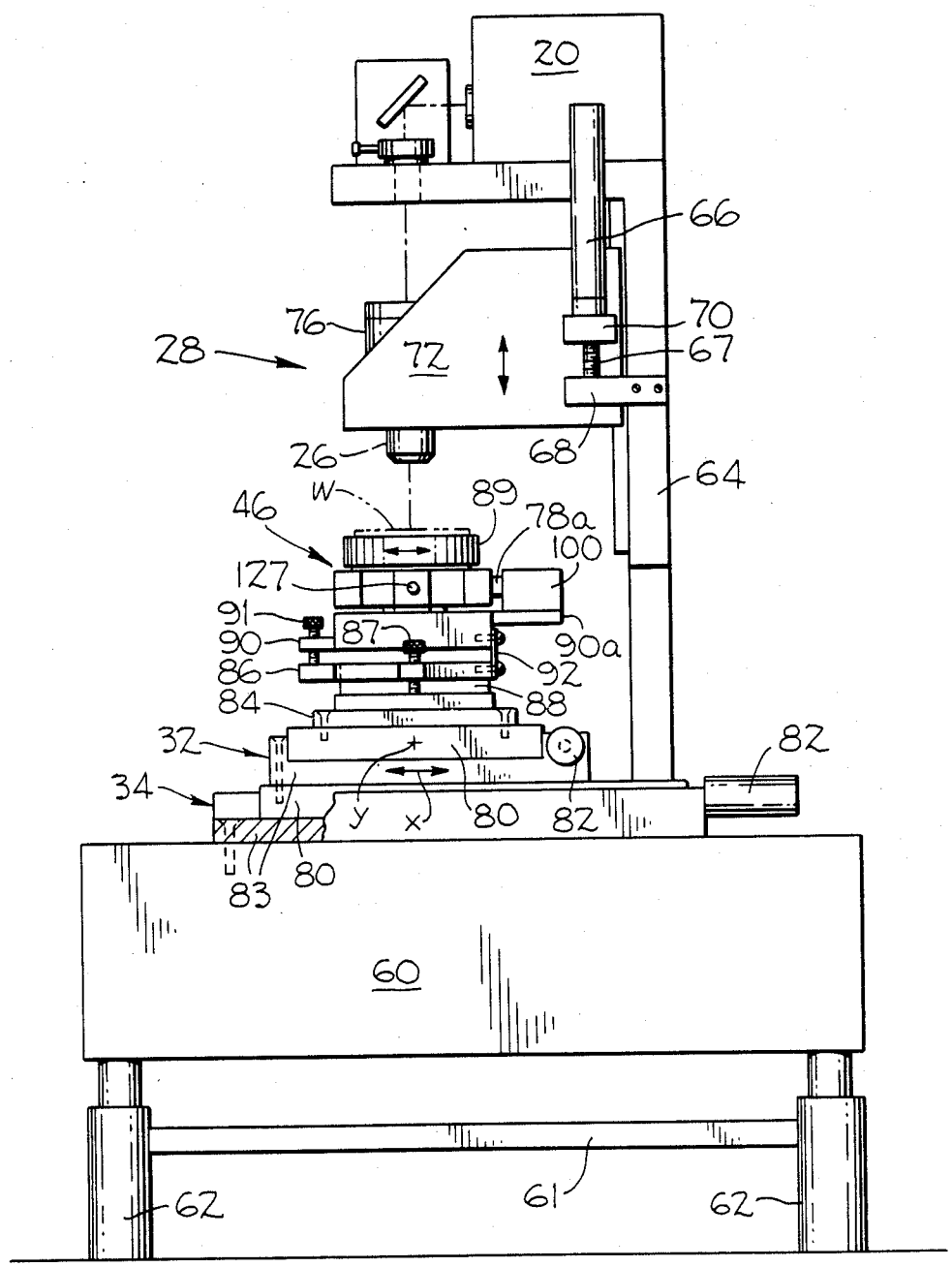
FIG. 2 is a side elevation, partially in section, of the mechanical portion of the apparatus of the present invention.
Figure 3:
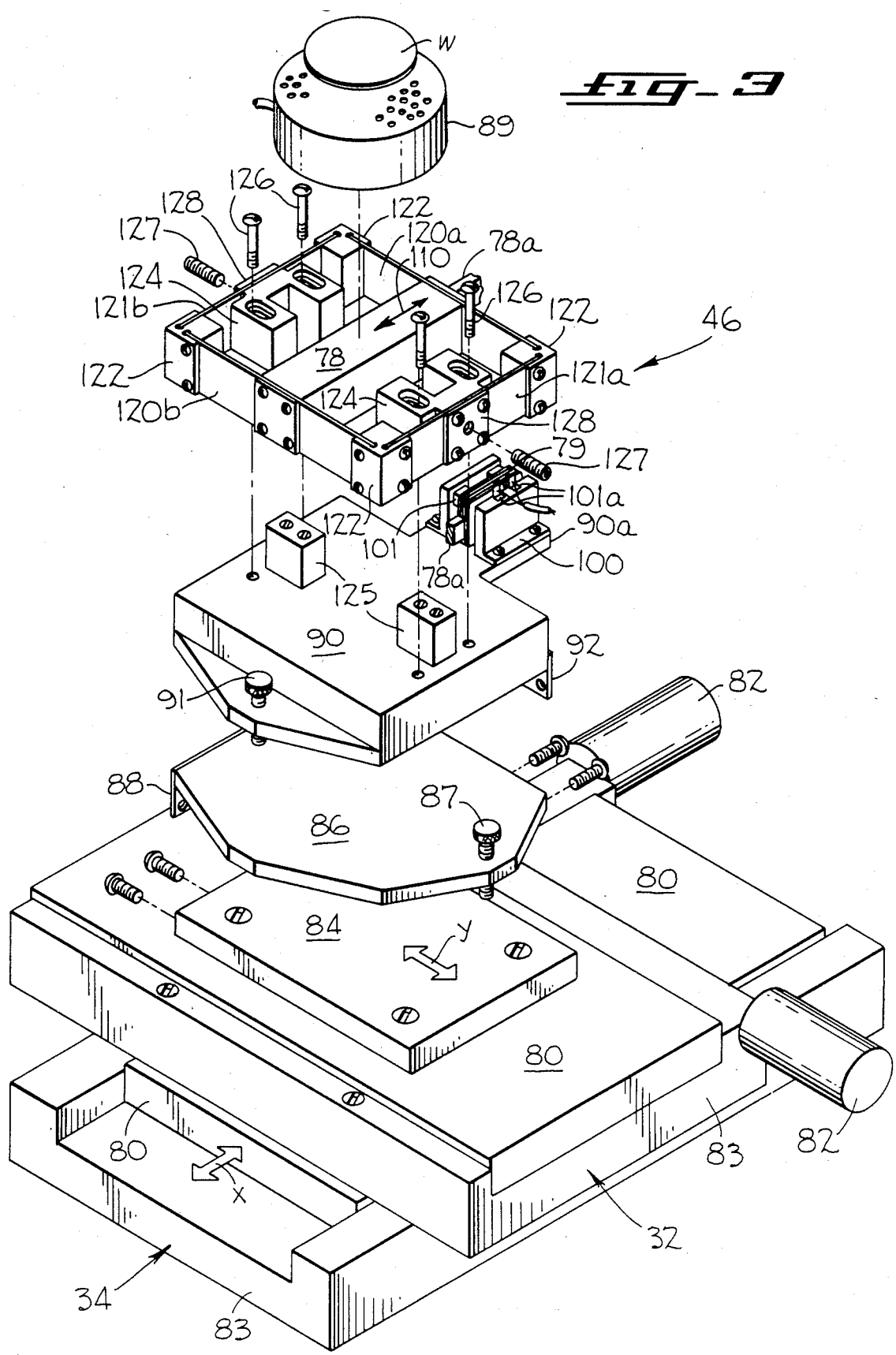
FIG. 3 is an exploded isometric view of the scanner and x-y planar drive mechanism of the system of the present invention.

The mechanical structure which comprises the semiconductor wafer scanning system is shown in FIGS. 2 through 5. Referring first to FIG. 3, it will be seen that the entire wafer drive apparatus and optical system is arranged to be mounted upon a large surface plate 60 which is seated upon a table 61 and isolated therefrom by four piston and cylinder type air springs 62 located so as to support each corner of the surface plate. A general frame structure 64 is elevated above the surface plate 60 to provide support for the optics module 20 including the vertically shiftable focus control mechanism 28.

Figure 4:
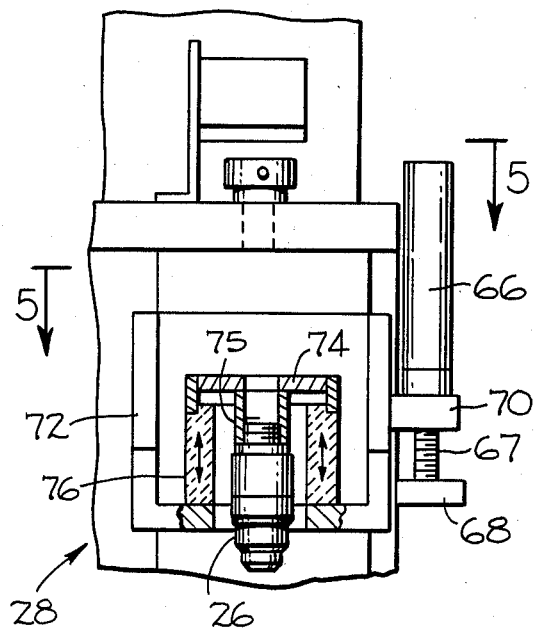
FIG. 4 is a front elevation, partially in section, of the focus control device of the apparatus of FIG. 2.
Figure 5:
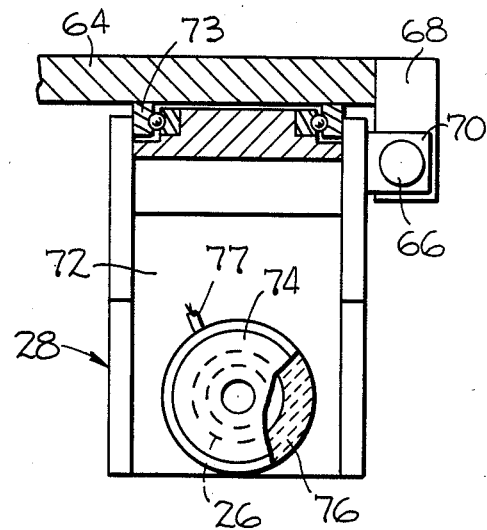
FIG. 5 is a section taken along line 5—5 of FIG. 4.

The details of the focus control mechanism are best shown in FIGS. 2, 4, and 5. The movable objective lens 26 will be seen to be mounted within a cage 72 open at the top and the front and with a back face (FIG. 5) adapted to slide within track 73 on the upright face of the frame structure 64. A support bracket 70 is attached to one side of cage 72 projecting outwardly therefrom to support a DC servo motor 66 with a projecting lead screw 67 thereof being adapted to engage the upper face of a support bracket 68 secured to a main upright portion of frame 64. It will be seen (from FIG. 2) that movement of the screw 67 within the motor assembly 66 serves to raise or lower the objective lens 26 relative to the underlying wafer support assembly. This lens movement is provided only for gross alignment of the optical system relative to the wafer surface, i.e., to move the optical system so that the surface of wafer w lies in the basic focal range of the optics. As will be explained presently, this gross movement will initially place the focal plane of the optical system close to but above the top surface of the wafer so that the lens 26 can thereafter be successively moved closer to the wafer as the beam from laser 40 is scanned across the wafer. Use of the motor 66 to elevate lens 26 well above the underlying wafer support structure also permits the wafer w to be readily loaded and unloaded.

The fine focusing (i.e., fine vertical adjustment) of the objective lens 26 is accomplished by means of a piezoelectric crystal 76 of generally cylindrical shape (FIGS. 4 and 5) which is attached between the base of the cage 72 and an overhead annular support member 74 which has a central hub 75 to which the upper end of the mount for lens 26 is threaded (FIG. 4). By varying the voltage to the electrical lead 77 (FIG. 5) the crystal 76 may be axially contracted or expanded in the direction of the arrows (FIG. 4) so as to, in turn, lower or elevate the objective lens 26 relative to the underlying wafer. It will be appreciated that the movement of lens 26 during the application of different electrical potentials to crystal 76 will be in the submicron range (e.g., 0.01 microns per increment) so that relatively small differences in surface levels on the face of the wafer are capable of being distinguished.

The planar (i.e., x-y) drive arrangement is best shown in the exploded view of FIG. 3. It will therein be seen that each of the x and y drive devices or stages 34, 32 is comprised of a conventional precision translation table which, in the presently described embodiment of the invention, is designed to have about six to eight inches of linear travel. These tables each include a drive motor 82 which serves to drive a slide block 80 within a channel shaped frame 83 by means of a lead screw (not shown) which is threaded to a nut attached to the slide block 80. Although not shown, it will be appreciated that each translation table includes an optical position encoder therein with submicron resolution and accuracy which serves to feed continuous position signals back to the computer 22 so that the precise position of the wafer in the x-y plane at any given time can be controlled and correlated with the reflected intensity measurements from the optical system during the operation of the apparatus. A flat lower tilt plate 84 is attached to the upper face of the slide block 80 of the upper, or y, stage translation table 32, and a middle tilt plate 86 is secured thereto by means of a leaf spring 88 which is rigidly bolted to the adjacent spaced ends of both of the tilt plates. A tilt adjusting screw 87 is threaded through the end of tilt plate 86 opposite to the mounting of spring 88 so as to bear against the upper surface of the lower tilt plate 84 so that the middle tilt plate (and the structure supported thereabove) can be tilted about the x-axis by adjustment of the screw 87. In a similar manner, an upper tilt plate 90 is secured in spaced relationship to the middle tilt plate 86 by means of a leaf spring 92 bolted to their rearward edges, and a tilt adjusting screw 91 is threaded through the forward edge of tilt plate 90 to bear against the upper surface of tilt plate 86 so as to adjustably rotate the tilt plate 90 about the y axis. It will be understood that in setting up the apparatus initially and checking it thereafter, it is essential that the tilt screws 87 and 91 are properly adjusted to insure that the surface of upper tilt plate 90 lies in a perfectly horizontal plane precisely perpendicular to the path of the light beam from the overhead optical system 20.

The vibratory scanner mechanism 46, by which the wafer w is rapidly vibrated in the direction of the x-axis, is shown in detail in FIG. 3. It will be seen that the scanner mechanism comprises a rectangular structure including a pair of leaf springs 120a and 120b for supporting for vibratory movement a drive bar 78, and a pair of tension adjusting leaf springs 121a, and 121b. The springs are arranged in a rectangular structure by attachment to four corner blocks 122 with the ends of each of the springs being tightly bolted to the corner blocks. The solid drive bar 78 is firmly attached to and extends between the midpoints of each of the vibratory leaf springs 120a and 120b. Positioned atop the drive bar 78 (see FIG. 2) is a vacuum chuck 89 which is supplied with a vacuum to hold the wafer w securely upon its flat upper surface. The rearwardly projecting end 78a of the drive bar 78 mounts a coil 79 to which a drive current is applied from the control circuitry 44 through amplifier 47 (FIG. 1) A plurality of fixed magnets 101 are mounted upon spaced upright mounting blocks 100 between which the coil 79 is positioned so as to complete the electromechancial drive arrangement for the scanner. The mounting blocks 100 are positioned upon and secured to an extension 90a of the upper tilt plate 90, as shown in FIG. 3, and also serve to mount the terminals 101a through which the coil 79 is connected to the drive circuitry. In order to rigidly secure the scanner 46 to the upper tilt plate 90. U-shaped mounting blocks 124 are bolted to the midpoint of each of the tensioning springs 121a, 121b through attachment plates 128. Each of the attachment plates has a threaded hole in the center thereof for receiving a set screw 127. Each screw extends freely through a passage in the associated U-shaped mounting block 124. Abutment blocks 125 are fixedly secured to the upper face of upper tilt plate 90 and provide surfaces against which the set screws 127 abut. Each mounting block 124 is also secured upon the upper face of upper tilt plate 90 by means of bolts 126 which are received in slots extending through the blocks so that loosening of the bolts permits the blocks to be shifted laterally with respect to the scanner. It will be appreciated that the mounting blocks 124 are thus free to slide upon the lateral faces of the abutment blocks 125 before the bolts 126 are fully tightened thereby permitting the tension springs 121a, 122b to be bowed outwardly from their innermost positions. This is done in order to apply the proper amount of tension in the leaf springs 120a and 120b so as to adjust the mechanical resonant frequency of the system to that desired. This mechanical resonant frequency should be set just slightly higher than the operating or drive frequency of the system so that the system will be energy efficient but so that the oscillatory drive will never pass through the resonance point wherein loss of control and damage to the structure could occur. It will be seen that by rotating the set screws 127 to move the plates 128 outwardly of the abutment blocks 125, the tensioning springs 121a, 121b bow outwardly to place an axial tensioning force on the springs 120a, 120b. Since each tensioning spring 121a, 121b can be adjusted separately through its associated set screw 127, it will be recognized that the separate adjustment of each side of the spring support system can be used to compensate for any asymmetry in the spring system construction to insure that a perfectly symmetrical drive arrangement is achieved.

It will be apparent that application of an alternating current to the coil 79 will shift the drive bar 78, and wafer w supported thereby, backwardly and forwardly in the direction of the x axis, i.e., in the opposed directions of arrow 110 (FIG. 3), at the frequency of the alternating current applied thereby bowing the support springs 120a, 120b accordingly. This lateral vibratory movement, which comprises the scan linewidth of the system along the x axis on the wafer, is set for a typical total excursion of about 2 millimeters.

The programming by which the computer system 22 controls the operation of the aforedescribed mechanical and optical apparatus of the present invention is shown in flow chart form in FIG. 6. Once the wafer w is appropriately positioned upon the vacuum chuck 89, the basic x-y planar drive mechanisms 34, 32 can be used to bring the wafer to a location beneath the optical imaging system 20 wherein the beam from laser 40 will overlie a particular site on the wafer. In a typical semiconductor wafer inspection operation, it is conventional to look at only a plurality of selected small areas or sites (e.g., 4) on the wafer rather than scanning the entire wafer because of the time limitations. Once the wafer has been moved so as to locate a starting x, y location within the first chosen wafer inspection site under the beam from the optical imaging system 20, by means of the x-y stage motor control circuitry 36 under command of signals from the computer 22, the focus control mechanism 28 is operated to bring the focus level to a focal plane $z_1$ which is chosen so that it will always be above the uppermost surface level of the wafer even if the wafer may vary somewhat in thickness or not lie in a perfectly horizontal plane (see the top figure in FIG. 8). The subroutine V(z) for obtaining and displaying a z (vertical) profile along a line (in the x direction) on the wafer is then carried out. This subroutine is shown specifically in FIGS. 7A, 7B, and 7C.

Figure 7A:
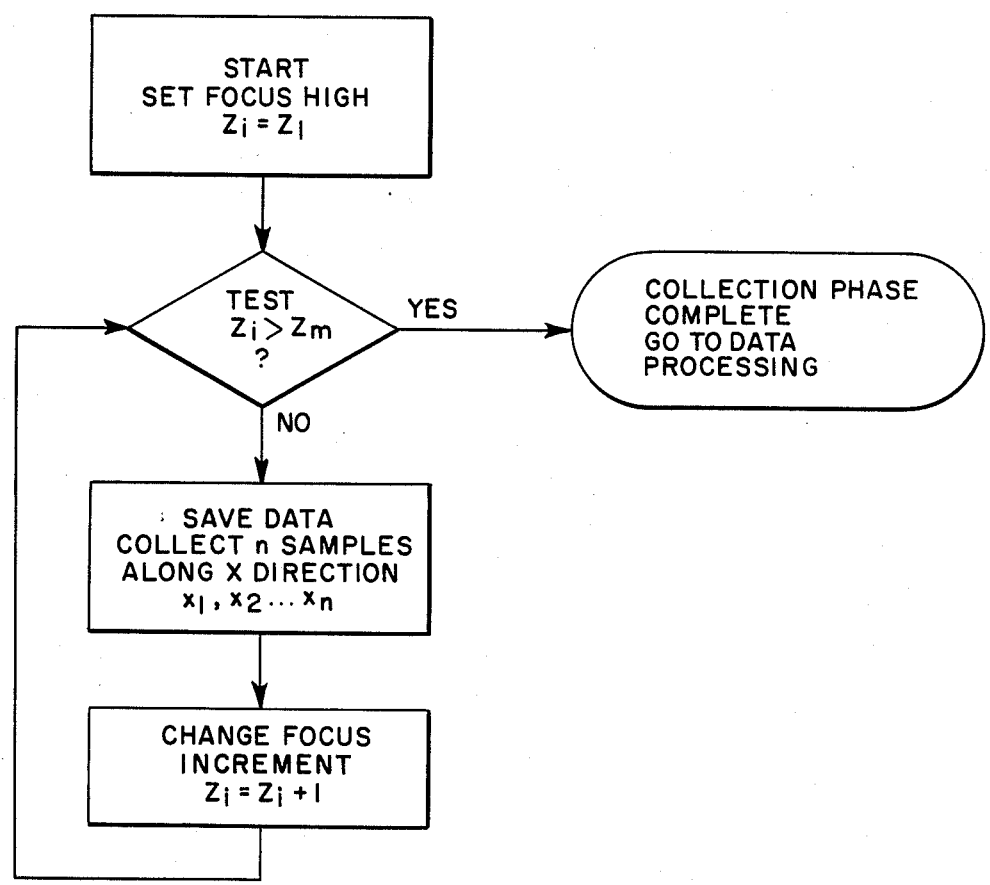

Referring first to FIG. 7A, the data collection phase, it will be seen that the focus control mechanism 28 is initially operated (through control circuitry 38) to bring the focal level of the optical system to its uppermost scanning level $z_1$ as explained previously. The vibratory scanning mechanism 46 is now operated to scan the beam from laser 40 along a line on the wafer while the control circuitry 44 (FIG. 1) samples the reflectivity data from photodetector 42 along the line at n samples (e.g., 512 samples) in a single (i.e., one-directional) scanning movement. These samples represent generally uniformly spaced positions ($x_1-x_{512}$) along the line from one lateral edge of the area or site to the other. As the spring system drive of scanner 46 brings the wafer back in the return direction along the scan line, no data is taken and the focus control mechanism 28 is operated to lower the focal level by an incremental distance (typically, a few hundredths of a micron). This procedure is repeated as the focal level (the z level) is successively lowered through m levels (e.g., 256 levels), as indicated in FIG. 7A, it being understood that at each level, 512 samples along the x direction will be obtained and all of this information will be stored within a memory in the computer system 22.

At the conclusion of the data gathering phase, the data will be processed in accordance with the programming shown in FIG. 7B. The data is saved within the computer in an array $x_i$ by $z_j$ wherein i (the spaced data taking positions along the x axis) will typically be about 512 while j (the incremental focal levels of the optical system) will typically be about 256. Thus, the data storage for the profiling operation must accommodate 512 by 256 or approximately 131K bytes of information. As shown in FIG. 7B, the system starts at $z_1$ and $x_1$ and looks for the maximum peak value ($P_m$) and the reflectivity signal (R) at such peak value and also looks for the first peak value $P_1$. Thus, at data position $x_1$ along the x axis, the program steps through each z level (1 through 256) successively testing the reflectivity values to first locate a first peak value (i.e., where the reflected intensity first rises to a peak value and then drops off) and then to locate a maximum peak value (i.e., the highest reflected intensity value). The maximum peak value will occur at that z level where the basic reflecting surface on the wafer lies precisely at the focal plane below the optical system, and the first peak (if there is a peak prior to the maximum value) will occur at that z level where a transparent or semi-transparent layer overlying the underlying basic reflecting surface lies precisely at the focal plane.

The foregoing process can be appreciated by the graphic illustrations of FIG. 8 which show a partial cross-sectional configuration for a typical wafer (in the uppermost figure) and the corresponding output displays for such profile provided in the graphics VDU 24b (FIG. 1). Thus, it will be seen that with an underlying base layer of silicon at a base layer A, a pair of spaced metallic lines of aluminum are provided at a level B and a higher insulating line of silicon dioxide is provided at a level D. Overlying the conductive and insulative material are some photoresist material of semi-transparent nature left after the etching process. The photoresist on the aluminum lines lies in a mound centered about level C while the photoresist on the silicon dioxide is at a uniform level E as shown. Thus, assuming that the data taking position $x_{10}$ is being processed and that this position lies within the silicon dioxide layer, as shown in FIG. 8, it will be appreciated that as the z levels are successively sequenced by the programming, that z level representing a focal plane at level E will provide a first peak reflectivity (R) value. As the z level approaches E, there will be a rise in the level of the corresponding signal R until it peaks at level E and then begins to drop off as the focal plane drops below level E. As the focal plane (z level) approaches level D however, another peak in the reflectivity signal is generated and this peak will be higher than the peak at level E since the silicon dioxide at D is a non-transparent layer of rather dull material but reflecting a much greater percentage of light then did the semi-transparent layer of photoresist at level E. As the focal plane or z level drops below level D, several other spurious peaks in the reflectivity signal may be generated of considerably smaller value than the peak at level D for optical reasons unimportant to an understanding of the present invention. Such peaks can be ignored. As shown in FIG. 7B, the computer will store the z level value ($z_j$) for the $x_{10}$ position and also the reflectivity value R at the maximum peak $P_m$. This process is repeated for each position along the x-axis. i.e., $x_1$ to $x_{512}$, with all of the foregoing information being recorded at each data taking position. For example, with reference to FIG. 8, it will be noted that at the $x_{90}$ position there will be no first peak separate from the maximum peak since only the silicon substrate level (at A) will reflect any light. Hence, at $x_{90}$ the system will not store a separate $P_1$ value.

The lower three graphs of FIG. 8 show the data display which is provided on the graphics video display unit 24b in three separate arrays. The upper graph represents z (depth at the wafer surface as referenced to the optical system) vs. x (linear location across the scan area). Referring now to the data display programming of FIG. 7C, it will be seen that the stored data (FIG. 7B) is utilized so that for each x position, each z level at which a maximum reflectivity signal was obtained is plotted and connected by a solid line. It will be recognized that this solid line comprises the z-axis profile or cross-sectional profile of the wafer surface as shown in the top illustration of FIG. 8. The reflectivity at each maximum signal position is also plotted on a separate graph (R vs. x) as shown in FIG. 8 and connected by a solid line. Referring to this graph, it will be seen that the reflectivity for the highly reflective aluminum lines is considerably greater than that of the silicon dioxide line—as would be expected. Finally, referring again to the top graph (z vs. x), the first peak (where one was found distinct from the maximum peak) is plotted in dotted lines. As shown in FIG. 8, the dotted line plots are only found overlying the conductive and insulative superimposed lines therein since these are the only positions where multiple reflective layers of material are found.

It will be seen from the R vs. x graph of FIG. 8 that the underlying silicon substrate level has a relatively low reflectivity; the silicon dioxide layer has a higher reflectivity level; and the metallic aluminum layers exhibit the highest reflectivity levels. The wavy surface of the aluminum lines reflects the granular metallic nature of the relatively flat metallic surface which inherently has variable reflectivity levels therein.

Figure 7C:
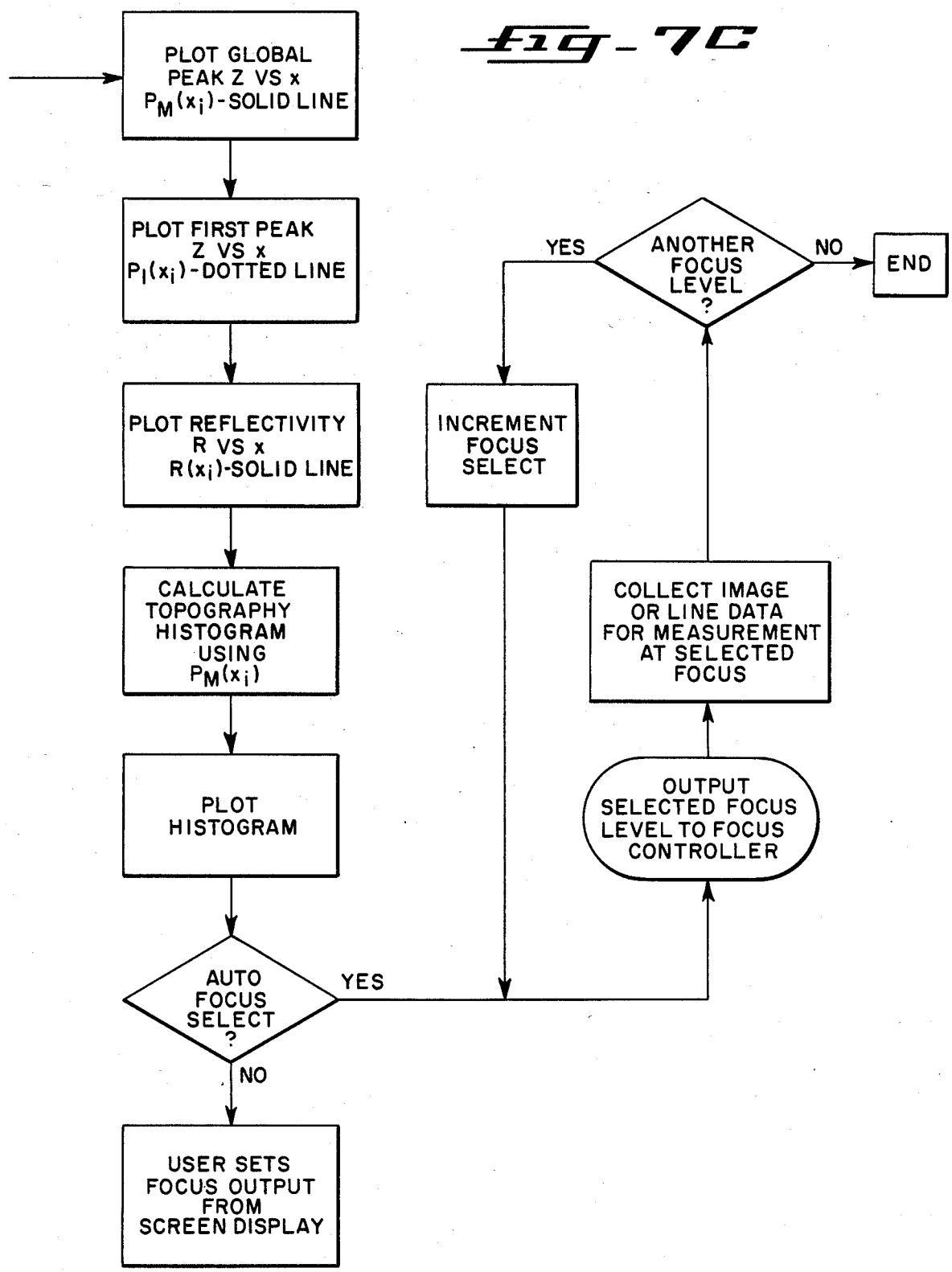

Finally, a histogram is calculated and plotted as indicated in FIG. 7C and as shown in the lowermost graphical display in FIG. 8. The histogram utilizes the same data used in the uppermost graph (z vs. x), but it is plotted in a different manner. Thus, the number of pixels, i.e., x positions $x_1$–$x_{512}$ found at each z level where a maximum reflectivity signal was observed are plotted. Comparing the upper and lower graphs of FIG. 8 it will be seen that the lowermost level A has the highest number of pixels while the level of the metallic lines B has the next highest and that all of these pixels are closely centered about the A and B elevations. It will be noted that a bell-shaped curve is formed about the C level: such curve representing the photoresist material capping the aluminum layers with the peak representing the average level of such material. Finally, the D and E levels are the smallest and are appropriately spaced at the relatively highest focal depth levels. The significance of preparing and displaying such a histogram is that either operator selection or conventional computer graphical analysis techniques can be utilized to locate each of the indicated peaks (A-E) which represent the specific levels of interest for scanning on the semiconductor wafer surface. Thus, as indicated in FIG. 7C, the automatic focusing function can be activated, wherein the z level at each clearly definable peak in the histogram will be selected for scanning, or the user can select only such levels as desired for further scanning. The system will thereafter be operated so that the focus control mechanism 28 will move the optical system to focus only on such selected levels rather than scanning the entire site area at each individual z level. In this way the z vs. x profile is utilized in an effective manner so that an entire site, i.e., the entire two-dimensional array of x and y positions may be scanned to obtain the three-dimensional representation but only at a few selected depth levels without losing any relevant information and while keeping the amount of stored data during one scan at a manageable level.

As indicated in FIG. 7C, when the automatic focus selection function is activated, the automatically selected focus levels can be set and sequentially fed to the focus control circuitry 38 (FIG. 1) prior to each complete two dimensional scan at a given z level. When all of the selected z levels at a particular site have been scanned, the system is ready to rapidly shift the position of the wafer relative to the optical system (by translation stages 32, 34) so that a new site or area underlies the vibratory scanning area of the optical system, and the process can be repeated.

Returning now to the flow chart of FIG. 6, which provides for the location of the z levels to be scanned where the user selects such levels, it will be seen that a nominal focus level ($z_{nom}$) is selected as the uppermost detectable layer on the wafer; for example, in the wafer cross-section of FIG. 8, top level E would represent the nominal focus level as indicated. Then each level of interest for scanning at or below level E would be defined by a focus offset or $\Delta z_j$ value with $\Delta z_j$ being defined as $z_{nom}$ minus the z level of scanning interest (e.g., level A, B, C, etc.). In the example provided level E would be set at $j=1$ and the $\Delta z_1$ value would be equal to 0 since level E is at the nominal focus level. Level D would be set at $j=2$ and the $\Delta z$ value would equal the incremental z distance between D and E. In a similar manner each of the other j values (j3–j5) would be set for levels C, B and A with the offset ($\Delta$) values being set at the corresponding z level differential with level E. These focus offsets $\Delta z_j$ are thus determined and stored. Then, with j being initially set equal to one, the focus control mechanism 28 is operated to move the focal plane to the first focal level 1or not moved at all if, as in the present case, the upper level of interest is at the nominal focus level (where the scanning operation will start), and the wafer area is scanned in the x, y plane in the manner previously described and as set forth in the aforementioned copending patent application Ser. No. 725,082. That is to say, the scanning mechanism 46 is operated in conjunction with a slow movement of y stage 32 so that reflectivity data is obtained for a matrix of closely spaced x positions and y positions throughout the scanned level. The reflectivity measurements R which are made at each of the x, y positions at the single z level can then be utilized for making linewidth measurements by noting the sharp changes in reflectivity levels and determining the distance therebetween in terms of the incremental x positions. Then, assuming that more z levels are to be scanned at the wafer site, the j value is increased by one, the control mechanism is operated to lower the focal plane, and the process is repeated until scanning has been accomplished at each of the selected focus offsets.

After the final, and lowermost, z level is scanned, the program moves to a new site on the wafer. This is accomplished by first asking the question whether more sites are to be scanned on the wafer and, if so, utilizing gross movements of x, y stages 34, 32 to shift the wafer to the new scanning position. Upon reaching the new site, the system first moves through an autofocus step. In this step, the focus control mechanism 28 is operated to first bring the focal level of the optics to the $z_1$ level known to be above the uppermost layer of the wafer. Then, the z level is successively lowered until a peak in the reflectivity signal R is recognized by the computer circuitry from the data supplied by line scan pixel memory 54 (FIG. 1). The successive lowering is accompanied by the sequential scanning of a line in the x direction and comparing the data with the previously received data ignoring any signals below a given threshold value (to eliminate the effects of noise). Once a peak is recognized (as distinguished from a random spike or other spurious signal), the optical system will be at the nominal focus level, i.e., $z_{nom}$, with respect to the wafer surface (see FIG. 8). At this level, the aforedescribed scanning program will be repeated wherein the optical system will be vertically moved only to the selected levels of interest with a complete scan in the x, y plane at each such level being obtained. It will be recognized that autofocusing is needed as the wafter is shifted to permit a separate site thereon to be scanned since the mounting of the wafer on the scanner 46 might not set the wafer in a true horizontal plane, and, in addition, the etched top surface of the wafer might not be truly flat: hence, refocusing to find a known reference level at each new site is generally necessary. However, it will be noted that it is not necessary to collect new profiling V(z) data at each new site since the previously generated focus offsets ($\Delta z_j$) will generally remain constant.

While linewidth measurements can be made, as in the aforedescribed process, simply by noting the x spacing difference between distant reflectivity signal changes on any given scan level, a better and more accurate way of measuring linewidths can be accomplished by utilizing the z vs. x profile display of FIG. 8. Since the data used to form this z vs. x graph is the maximum reflectivity signal at each individual x position along the scanning line, errors due to focusing problems, particularly at the edges of a line where the contour of the surface is changing, will be minimized. Conventional computer linewidth measurement techniques are utilized to actually make the measurements with the computer system 22 of the present invention. For example, with respect to the profile shown in FIG. 8, the first (silicon dioxide) line can be automatically recognized, the top and bottom levels thereof (D and A) defined, and a predetermined percentage (e.g., 50%) therebetween utilized as a defined measuring point. Then, it is a simple matter to determine the distance between the thus defined measuring points at the leading and trailing edges of the line in terms of the number of x positions therebetween. Standard interpolation methods can be utilized to improve the accuracy of the measurements by defining the measuring points in terms of fractions of an x position spacing (i.e., pixel width). As explained previously, the x positions are generally uniformly spaced across the wafer at known (e.g., submicron) spacings.

The programming process to find the "superfocus" image is illustrated in the flow chart of FIG. 9. The "superfocus" image is the image of an entire scanned site or area on the wafer surface utilizing the information obtained by focusing the optical system at different levels. The image is displayed in the image display monitor 24a (FIG. 1) after the correct signals for the two dimensional video matrix are determined by the computer system 22 and stored in the video display memory 29. Once the wafer is moved so that the optics focus on the applicable site on the wafer, the V(z) data (for making the initial profile) is collected along a scan line at the center of the scanning field. This means that the x scanning line utilized is one halfway down the x-y maxtrix which is to be ultimately displayed in monitor 24a. The x-z profile is then obtained in the manner previously described, and a V(z) histogram (as in FIG. 8) is generated and displayed. The computer next asks the question whether or not the data provided by scanning along a single line is sufficient. For example, if the pattern within the entire x-y frame includes features which cannot be captured in a single x-line scan, then the y stage 32 must be driven to move the scanning mechanism 46 to a new location to provide a second x-line scan. This generates a new z profile which can be utilized for making linewidth measurements, and the z data obtained therefrom is simply added to the previously stored data in the histogram generating subroutine so that the data therein is accumulative. Thus, if there is a level found in the second x-line scan which was not present in the first x-line scan, a wholly new peak will be formed in the histogram. When it is determined that all of the necessary information has been obtained by a sufficient number of x-line scans, the program moves on to the process of obtaining the superfocus image.

First, the main peaks (or z levels of interest) in the histogram are identified in the manner previously pointed out. This can be done manually by the operator or accomplished by conventional computer analysis techniques. The focus control meachanism 28 then moves the optical imaging system to focus on the first peak, i.e., the first level of interest, and the entire x-y plane is scanned and the data recorded. This data is stored in a buffer, and the focus control mechanism moves the imaging system to focus at the second peak, i.e., the second level of interest wherein the process is repeated with the new data being added to the previously stored data in the buffer. This process continues until each level of interest is scanned with all of the data for each x, y position being accumulated in a plurality of x, y matrices. The data can then be displayed as a single plane of data on the image display monitor 24a with the data for any given (x, y) point on the screen being derived from the accumulated information from all of the scanned levels.

As one method of display of the superfocus image, it is possible to color code each individual level and display the maximum intensities at any given x, y position in accordance with the color coded level. This will produce a multi-color image with the different colors representing the different surface levels on the wafer. A second method of display involves simply adding all of the R signal values obtained at the different scan levels for each x, y position. An alternative to the foregoing method of display to improve the sharpness and quality of the image is to add the different R signal values for each x, y position but set a threshold level for each scan plane so that the grossly out-of-focus data would be set to zero. This threshold level could vary from plane to plane so that the sharpest possible image would be provided. Another alternative method of display would be to use only the maximum reflectivity signal at each x, y position so that the generated display image represents the x, z profile of FIG. 8 taken at each y level of the composite x, y matrix. The actual z vs. x profiles for each such y level could also be generated and stored. Such data could be displayed either graphically in a isometric (x, y, z) plot or used to modulate the intensity at each x, y position in a two dimensional display.

From the foregoing it will be seen that the initial generation of a z-axis profile or cross-sectional image of the wafer surface permits all of the relevant wafer scanning data to be subsequently obtained in a rapid and highly efficient manner. First, direct linewidth measurements can be made directly from the z-axis profile more easily and more accurately than by utilizing conventional linewidth scanning techniques. Secondly, the initial generation of a z-axis profile by the computer permits a ready analysis (either by the operator or automatically by the apparatus) after scanning a single line (or a few lines) to develop the program for scanning a complete site or area on the wafer surface so that the computer time and storage capacity is used most effectively. This is accomplished by first identifying and then scanning only those particular levels of interest which provide all of the information necessary for providing a complete topographical image of the surface of the semiconductor wafer.

Although the best modes contemplated for carrying out the present invention have been herein shown and described, it will be apparent that modification and variation may be made without departing from what is regarded to be the subject matter of the invention.

What is claimed is:

1. A method of obtaining a representation of the surface profile of a portion of a specimen such as a semiconductor wafer comprising the steps of projecting a sharply defined beam through a confocal optical imaging system having a very narrow depth of field to focus it into a small spot upon the wafer surface and detecting a measurable characteristic of the beam reflected from said spot, relatively moving the projected beam and the wafer so that the spot scans a line on a portion of said wafer, recording and storing a signal with respect to said measurable characteristic at a plurality of closely spaced positions along said line, successively changing the relative spacing between the imaging system and the wafer by a small incremental distance after each scan of said line such that the focus level of the system with respect to the wafer surface is successively changed by said incremental distances in a given direction perpendicular to said scan line, and separately determining the relative spacing level for each of said points along said line at which a signal most characteristic of a surface indication was obtained to provide a cross-sectional representation of the surface of the wafer along said line.

2. The method of claim 1 wherein the focus level is initially set above the uppermost surface of the wafer and is successively lowered by said incremental distances through the entire surface profile.

3. The method of claim 1 wherein the measurable characteristic of the beam comprises its intensity and wherein the spacing levels for providing the cross-sectional representation along said line are determined in accordance with the maximum detected intensity of the reflected beam at each of said closely spaced positions.

4. The method of claim 3 wherein said optical imaging system is fixed in position except for changes in its focal depth and the wafer is moved in a plane beneath the imaging system to obtain said line scan.

5. The method of claim 4 wherein the step of changing the relative spacing between the imaging system and the wafer is accomplished by shifting the vertical position of an objective lens in the imaging system.

6. The method of claim 1 including the step of displaying a graph of the cross-sectional representation for permitting an observer to make decisions with regard to further scanning of the wafer.

7. A method of scanning semiconductor wafers or the like for determining surface pattern information in a given area on the wafer comprising the steps of projecting a sharply defined beam through a confocal optical imaging system having a very narrow depth of field to focus it onto a small spot within said area upon the wafer surface and detecting a measurable characteristic of the beam reflected from said spot, relatively moving the projected beam and the wafer so that the spot scans a line across said area of said wafer, recording and storing a signal with respect to said measurable characteristic at a plurality of closely spaced positions along said scan line, successively changing the relative spacing between the imaging system and the wafer by a small incremental distance after each scan of said scan line such that the focus level of the system with respect to the wafer surface is successively changed by said incremental distances in a given direction perpendicular to said scan line, separately determining the relative spacing level for each of said points along said scan line at which a signal most characteristic of a surface indication was obtained to provide a cross-sectional representation of the surface of the wafer along said scan line, selecting from said cross-sectional representation those levels which provide the maximum surface pattern information, and scanning the remainder of said area by relatively moving the beam and the wafer over a plurality of lines parallel to said scan line at each of the selected levels while recording and storing said signals to thereby obtain all of the relevant surface pattern information within said area of the wafer.

8. The method of claim 7 wherein the focus level is initially set above the uppermost surface of the wafer and is successively lowered by said incremental distances through the entire surface profile.

9. The method of claim 8 wherein said optical imaging system is fixed in position except for changes in its focal depth and the wafer is moved in a plane beneath the imaging system to obtain said line scan.

10. The method of claim 9 wherein the step of changing the relative spacing between the imaging system and the wafer is accomplished by shifting the vertical position of an objective ens in the imaging system.

11. The method of claim 7 wherein the measurable characteristic of the beam comprises its intensity and wherein the spacing levels for providing the cross-sectional representation along said scan line are determined in accordance with the maximum detected intensity of the reflected beam at each of said closely spaced positions.

12. The method of claim 7 including the step of displaying a graph of the cross-sectional representation for permitting an operator to perform the selecting step.

13. The method of claim 12 including the step of providing a two dimensional image of said given area on the wafer by adding the signal values obtained at each selected level for each of the closely spaced positions of all of the parallel scan lines.

14. The method of claim 13 including the step of setting certain of the signal values to zero prior to the adding step if such certain signal values indicate that they represent reflections from surfaces substantially out of focus of the imaging system.

15. The method of claim 12 including the step of providing a two dimensional image of said given area on the wafer by determining the maximum signal value of the selected scanning levels at each of the closely spaced positions of all of the parallel scan lines.

16. A method of making linewidth measurements on the surface of a semiconductor wafer or the line comprising the steps of projecting a sharply defined beam through a confocal optical imaging system having a very narrow depth of field to focus it onto a small spot upon the wafer surface and detecting a measurable characteristic of the beam reflected from said spot, relatively moving the projected beam and the wafer so that the spot scans a line on a portion of said wafer, recording and storing a signal with respect to said measurable characteristic at a plurality of closely spaced positions along said line, successively changing the relative spacing between the imaging system and the wafer by a small incremental distance after each scan of said line such that the focus level of the system with respect to the wafer surface is successively changed by said incremental distances in a given direction perpendicular to said scan line, separately determining the relative spacing level for each of said points along said line at which a signal most characteristic of a surface indication was obtained, providing a cross-sectional representation of the surface of the wafer along said line by connecting the points determined by said line, and measuring across the distance between the generally vertical portions of said cross-sectional representation to obtain the linewidths of a superimposed pattern of the wafer surface.

17. The method of claim 16 wherein the focus level is initially set above the uppermost surface of the wafer and is successively lowered by said incremental distances through the entire surface profile.

18. The method of claim 16 wherein the measurable characteristic of the beam comprises its intensity and wherein the spacing levels for providing the cross-sectional representation along said line are determined in accordance with the maximum detected intensity of the reflected beam at each of said closely spaced positions.

19. The method of claim 16 wherein said optical imaging system is fixed in position except for changes in its focal depth and the wafer is moved in a plane beneath the imaging system to obtain said line scan.

20. The method of claim 16 wherein said cross-sectional representation is provided in the form of a graph for permitting an operator to make said measurements for obtaining linewidths.

21. A system for determining the cross-sectional profile of a specimen such as a semiconductor wafer comprising a confocal optical imaging system having a very narrow depth of field for focusing a beam on a small spot on an underlying wafer and including a photodetector for receiving the reflected spot from the wafer for detecting a measurable characteristic thereof and providing an output signal, means for effecting relative movement of a rapid oscillatory nature between the imaging system and the wafer in a plane parallel to the surface of the wafer such that the spot repeatedly scans along a line across a portion of the wafer,
- means for obtaining and storing said photodetector signal at a plurality of closely spaced points in a single one-directional scan along said line,
- means for successively shifting the focus of said imaging system with respect to the wafer by an incremental distance after each one-directional scan along said line during the return relative movement of the system and wafer,
- means for determining the focus level for the imaging system at which the maximum output signal is obtained for each of said spaced points along said line,
- and means for providing said focus levels as determined by said last named means as a representation of the cross-sectional profile of said wafer along said line.

22. A system according to claim 21 wherein the measurable characteristic of the beam comprises its intensity, said focus level determining means determining the maximum intensity as a representation of the maximum reflectivity for the scanned levels at each point along said line.

23. A system according to claim 21 wherein said means for effecting relative movement comprises means for oscillating said wafer in a linear path.

24. A system according to claim 21 wherein said imaging system includes an objective lens and said means for shifting the focus of the imaging system includes means for altering the spacing between said objective lens and the wafer along the path of the beam.

25. A system according to claim 21 wherein said means for providing the determined focus levels comprises a graphical output display wherein the determined focus levels are connected in a continuous line defining the cross-sectional profile of the wafer.

26. A system according to claim 21 including means for determining separate surface levels along the scanned wafer surface by providing from said means for providing the determined focus levels a histogram of the various focus levels versus the number of points along said line at which said focus levels were found.

27. A system for determining the cross-sectional profile of a specimen such as a semiconductor wafer comprising means for mounting said wafer for oscillatory scanning movement along a line in a plane generally parallel to the surface of the wafer; a confocal optical imaging system having a very narrow depth of field overlying said wafer, said imaging system including a light source, means for directing the beam from the light source perpendicularly to the wafer surface and focusing it on a spot on the wafer, and photodetector means for receiving the light reflected from the spot and providing an output signal varying in accordance with the intensity of the reflected spot; means for incrementally moving at least a portion of said imaging system in a direction substantially perpendicular to said plane to successively change the focal length of the imaging system by a small amount relative to the surface profile of the wafer; means for recording said output signals at times corresponding to a plurality of closely spaced positions along said line during each scanning movement of the wafer; means connected to said recording means for determining the focal depth at which the maximum output signal was received at each of said closely spaced positions; and means connected to said last named means for providing the surface profile of said wafer along said line as represented by the focal depth determined for each of said positions.

28. A system according to claim 27 wherein said means for providing the surface profile comprises a graphical output display wherein the focal depth positions are connected in a continuous line defining the cross-sectional profile of the wafer.

29. A system according to claim 27 including means for determining separate surface levels along the scanned wafer surface by providing from said means for providing the surface profile a histogram of the various focal depths versus the number of positions along said line at which said focal depths were found.

30. A system according to claim 27 wherein said imaging system includes an objective lens and said means for moving at least a portion of said imaging system comprises a piezoelectric crystal operatively connected to said objective lens, and means for varying the voltage applied to said crystal to cause it to expand or contract and thereby shift the spatial position of said objective lens.

31. A system for scanning semiconductor wafers or the like for determining surface pattern information in a given area on the wafer comprising a confocal optical imaging system having a very narrow depth of field for focusing a beam on a small spot on an underlying wafer and including a photodetector for receiving the reflected spot from the wafer for detecting a measurable characteristic thereof and providing an output signal, means for effecting relative movement between the imaging system and the wafer such that the spot scans along a line across a portion of the wafer,
  means for obtaining and storing said photodetector signal at a plurality of closely spaced points in a single scan along said line,
  means for successively shifting the focus of said imaging system with respect to the wafer by an incremental distance after each scan along said line,
  means for determining the focus level for the imaging system at which the maximum output signal is obtained for each of said spaced points along said scan line,
  means for providing said focus levels as determined by said last named means as a representation of the cross-sectional profile of said wafer along said scan line,
  means for selecting from said representation of the cross-sectional profile those levels which provide the maximum surface pattern information,
  means for thereafter causing the focus shifting means to shift the focus of the imaging system successively to each of the selected levels,
  and means for causing the means for effecting relative movement to scan over a plurality of lines parallel to said scan line while the focus level is at each of the selected levels to thereby scan the remainder of said given area on the wafer to obtain all of the relevant surface pattern information within said area.

32. A system according to claim 31 wherein the measurable characteristic of the beam comprises its intensity, said focus level determining means determining the maximum intensity as a representation of the maximum reflectivity for the scanned levels at each point along said line.

33. A system according to claim 31 wherein said means for effecting relative movement comprises means for oscillating said wafer in a generally linear path.

34. A system according to claim 33 wherein said means for causing the means for effecting relative movement to scan over a plurality of lines comprises a drive means operable to move the wafer at right angles to said linear path at a slow linear speed relative to the oscillatory speed of movement in said linear path.

35. A system according to claim 32 wherein said imaging system includes an objective lens and said means for shifting the focus of the imaging system includes means for altering the spacing between said objective lens and the wafer along the path of the beam.

36. A system according to claim 31 wherein said means for providing the determined focus levels acomprises a graphical output display wherein the determined focus levels are connected in a continuous line defining the cross-sectional profile of the wafer.

37. A system according to claim 31 wherein said means for selecting includes means for providing a histogram of the various focus levels versus the level of points along said line at which said focus levels were found.

38. A system for making linewidth measurements on the surface of a semiconductor wafer or the like comprising a confocal optical imaging system having a very narrow depth of field for focusing a beam on a small spot on an underlying wafer and including a photodetector for receiving the reflected spot from the wafer for detecting a measurable characteristic thereof and providing an output signal, means for effecting relative movement of a rapid oscillatory nature between the imaging system and the wafer in a plane parallel to the surface of the wafer such that the spot repeatedly scans along a line across a portion of the wafer, means for obtaining and storing said photodetector signal at a plurality of closely spaced points in a single one-directional scan along said line, means for successively shifting the focus of said imaging system with respect to the wafer by an incremental distance after each one-directional scan along said line during the return relative movement of the system and wafer, means for determining the focus level for the imaging system at which the maximum output signal is obtained for each of said spaced points along said line, means for providing a cross-sectional representation of the surface of said wafer by connecting the points determined by said last named means to form a continuous cross-sectional line, and means for measuring across the distance between the generally vertical positions of said cross-sectional line to obtain the linewidth of a superimposed pattern on the wafer surface.

39. A system according to claim 38 wherein the measurable characteristic of the beam comprises its intensity, said focus level determining means determining the maximum intensity as a representation of the maximum reflectivity for the scanned levels at each point along said line.

40. A system according to claim 38 wherein said means for effecting relative movement comprises means for oscillating said wafer in a linear path.

41. A system according to claim 40 wherein said imaging system includes an objective lens and said means for shifting the focus of the imaging system includes means for altering the spacing between said objective lens and the wafer along the path of the beam.

42. A system according to claim 41 wherein said means for providing a cross-sectional representation comprises a graphical output display wherein the determined focus levels are connected in a continuous line defining the cross-sectional profile of the wafer.

* * * * *